(12) United States Patent
Cabrera et al.

(10) Patent No.: US 9,649,484 B2
(45) Date of Patent: May 16, 2017

(54) SNAP CONNECTION FOR TWO TUBES

(71) Applicant: Covidien LP, Mansfield, MA (US)

(72) Inventors: Ramiro Cabrera, Cheshire, CT (US);
Anne Nelson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 327 days.

(21) Appl. No.: 14/190,649

(22) Filed: Feb. 26, 2014

(65) Prior Publication Data
US 2014/0291985 A1 Oct. 2, 2014

Related U.S. Application Data

(60) Provisional application No. 61/805,990, filed on Mar. 28, 2013.

(51) Int. Cl.
| | |
|---|---|
| *A61M 39/10* | (2006.01) |
| *F16L 37/12* | (2006.01) |
| *F16L 37/092* | (2006.01) |
| *F16L 37/088* | (2006.01) |
| *A61M 39/08* | (2006.01) |

(52) U.S. Cl.
CPC ............ *A61M 39/10* (2013.01); *A61M 39/08* (2013.01); *F16L 37/088* (2013.01); *F16L 37/092* (2013.01); *F16L 37/1225* (2013.01); *F16L 37/1235* (2013.01)

(58) Field of Classification Search
CPC ..... A61M 39/10; F16L 37/088; F16L 37/092; F16L 37/1225; F16L 37/1235
USPC ................ 285/305, 307, 308, 321, 394, 921
See application file for complete search history.

(56) References Cited

U.S. PATENT DOCUMENTS

| | | | | |
|---|---|---|---|---|
| 472,342 | A * | 4/1892 | Draudt et al. ........ | F16L 37/088 285/317 |
| 3,151,891 | A * | 10/1964 | Sanders ................ | F16L 37/088 285/110 |
| 3,603,619 | A * | 9/1971 | Bengesser ........... | F16L 37/0844 285/321 |
| 4,061,366 | A * | 12/1977 | Affa ...................... | F16L 37/505 285/305 |
| 5,423,776 | A | 6/1995 | Haindl | |
| 5,437,650 | A | 8/1995 | Larkin et al. | |
| 5,490,694 | A * | 2/1996 | Shumway ............. | F16L 37/088 285/276 |
| 5,507,733 | A | 4/1996 | Larkin et al. | |
| 5,509,911 | A | 4/1996 | Cottone, Sr. et al. | |

(Continued)

FOREIGN PATENT DOCUMENTS

| | | |
|---|---|---|
| WO | WO02/080780 | 10/2002 |
| WO | WO2005/087113 | 9/2005 |

*Primary Examiner* — Adriana Figueroa
*Assistant Examiner* — Jessie Fonseca

(57) ABSTRACT

A medical tube assembly is disclosed, and includes a first tube portion defining a longitudinal axis, a second tube portion, and a coupling member. The coupling member is configured to couple the first tube portion and the second tube portion. The coupling member is configured to circumferentially engage the second tube portion and has a protrusion configured to engage a portion of the first tube portion. The second tube portion is configured to transition the coupling member from a resting condition to a coupling condition. The coupling member is configured to engage the first tube portion in the coupling condition.

16 Claims, 5 Drawing Sheets

(56) References Cited

U.S. PATENT DOCUMENTS

| | | | |
|---|---|---|---|
| 5,876,071 A * | 3/1999 | Aldridge | F16L 37/088 285/305 |
| 5,882,044 A * | 3/1999 | Sloane | F16L 19/005 285/148.19 |
| 5,993,437 A | 11/1999 | Raoz | |
| 6,254,589 B1 | 7/2001 | Raoz | |
| 6,386,596 B1 * | 5/2002 | Olson | F16L 37/0925 285/305 |
| 6,423,053 B1 | 7/2002 | Lee | |
| 6,676,651 B2 | 1/2004 | Haacke et al. | |
| 6,929,289 B1 | 8/2005 | Guest | |
| RE39,499 E | 2/2007 | Racz | |
| 7,393,019 B2 * | 7/2008 | Taga | F16L 33/227 285/321 |
| 7,578,803 B2 | 8/2009 | Rome et al. | |
| 7,678,101 B2 | 3/2010 | Sage | |
| 7,722,089 B2 * | 5/2010 | Nauer | F16L 37/088 285/305 |
| 7,954,860 B2 * | 6/2011 | Suzuki | F16L 33/03 285/113 |
| 7,976,072 B2 * | 7/2011 | Parrish | H01R 13/5219 285/308 |
| 7,985,068 B2 * | 7/2011 | Burdsall | F16L 37/088 285/12 |
| 8,235,971 B2 | 8/2012 | Christensen et al. | |
| 9,016,385 B2 * | 4/2015 | Veit | E21B 43/04 166/242.6 |
| 2003/0032941 A1 | 2/2003 | Boyle et al. | |
| 2004/0215158 A1 | 10/2004 | Anderson | |
| 2005/0015075 A1 | 1/2005 | Wright et al. | |
| 2005/0192559 A1 | 9/2005 | Michels et al. | |
| 2005/0245898 A1 | 11/2005 | Wright et al. | |
| 2007/0026703 A1 * | 2/2007 | Taga | F16L 33/227 439/108 |
| 2007/0066965 A1 | 3/2007 | Coambs et al. | |
| 2007/0246936 A1 * | 10/2007 | Jeltsch | F16L 25/0045 285/319 |
| 2009/0157052 A1 | 6/2009 | Verbitsky et al. | |
| 2010/0140923 A1 * | 6/2010 | Hellfeier | F16L 37/088 285/24 |
| 2010/0145313 A1 | 6/2010 | Packard | |
| 2011/0148098 A1 * | 6/2011 | Flynn | F16L 25/01 285/145.2 |
| 2012/0041426 A1 | 2/2012 | Bizup | |
| 2012/0046648 A1 | 2/2012 | Scheckel | |
| 2012/0253322 A1 | 10/2012 | Barron et al. | |

* cited by examiner

SNAP CONNECTION FOR TWO TUBES

CROSS-REFERENCE TO RELATED APPLICATIONS

This application claims the benefit of and priority to U.S. Provisional Patent Application No. 61/805,990, filed Mar. 28, 2013, the entire disclosure of which is incorporated by reference herein.

BACKGROUND

1. Technical Field

The present disclosure relates to tube assemblies for use in medical procedures. More specifically, the present disclosure relates to a tube assembly incorporating multiple tube portions and a coupling member to couple the multiple tube portions together.

2. Background of Related Art

Various types of tube assemblies are known in the art, and are commonly used, for example, to transfer fluids to, from, and within portions of a human or animal. Tube assemblies, such as catheter tubes, are employed in, e.g., dialysis procedures, delivery of treatment fluids, and drainage.

Some tube assemblies incorporate multiple interconnected components, i.e., some tube assemblies include multiple tube portions that are interconnected to form a single structure. Common coupling techniques for tube portions may include, e.g., press-fit, interference fit, bayonet-type coupling, and adhesion or welding. Challenges may be presented in coupling tube assemblies in urgent situations, given the challenges in maintaining a substantially fluid-tight seal between separable components. Accordingly, it is desirable to incorporate a coupling system into a tube assembly that facilitates ease of coupling and uncoupling of multiple components into a secure assembly. Thus, there is a need for an improved tube assembly incorporating a coupling member facilitating ease of coupling and uncoupling of multiple tube portions while maintaining a substantially fluid-tight environment therein, i.e., fluid leakage is minimized between tube portions.

SUMMARY

According to one aspect of the present disclosure, medical tube assembly is disclosed, and includes a first tube portion defining a longitudinal axis, a second tube portion, and a coupling member. The coupling member is configured to couple the first tube portion and the second tube portion. The coupling member is configured to circumferentially engage the second tube portion and has a protrusion configured to engage a portion of the first tube portion. The second tube portion is configured to transition the coupling member from a resting condition to a coupling condition. The coupling member is configured to engage the first tube portion in the coupling condition.

According to another aspect of the present disclosure, the first tube portion defines a cross-sectional diameter measured orthogonal to the longitudinal axis, and the second tube portion defines a different cross-sectional diameter measured orthogonal to the longitudinal axis. The first tube portion and the second tube portion may be configured to define a coextensive region upon coupling. The protrusion of the coupling member is configured to be disposed along the coextensive region upon coupling.

According to another aspect of the present disclosure, the first tube portion and the second tube portion are configured to be coupled in coaxial relation. In another aspect of the present disclosure, the second tube portion includes an aperture configured to receive the protrusion of the coupling member. According to a further aspect of the present disclosure, the coupling member is configured to be radially compressed. The coupling member may be configured to maintain a resilient bias toward a resting condition.

According to another aspect of the present disclosure, the second tube portion defines an interior chamfer. In another aspect of the present disclosure, the interior chamfer is oriented at an oblique angle with respect to the longitudinal axis. The interior chamfer may be configured to slidably urge the protrusion of the coupling member in a radially inward direction. According to another aspect of the present disclosure, the medical tube assembly may further include a sealing member. The sealing member is configured to minimize fluid leakage between the first tube portion and the second tube portion.

According to another aspect of the present disclosure, a medical tube assembly is disclosed, and includes a first tube portion, a second tube portion, and a coupling member. The first tube portion defines a longitudinal axis and an aperture through an outer wall thereof. The second tube portion is configured for insertion into the first tube portion. The coupling member is disposed around the second tube portion and includes a protrusion configured to fit within the aperture and is radially reconfigurable from a resting condition to a coupling condition in which the protrusion is disposed radially inward with respect to the resting condition. The protrusion is configured to extend through the aperture in the coupling condition.

In another aspect of the present disclosure, the coupling member is configured such that the coupling member is biased toward the resting condition. In a further aspect of the present disclosure, the second tube portion defines an internal chamfer configured to slidably engage the protrusion to reconfigure the coupling member from the resting condition to the coupling condition.

According to another aspect of the present disclosure, a method of coupling medical tubes is disclosed, and includes providing a first tube portion defining a longitudinal axis and an aperture in an outer wall thereof. The method also includes providing a second tube portion defining an interior chamfer. The method further includes providing a coupling member around the first tube, the coupling member including a protrusion configured to fit within the aperture. The method also includes inserting the first tube portion into the second tube portion such that the protrusion engages the interior chamfer to compress the coupling member and bias the protrusion into the aperture.

According to another aspect of the present disclosure, the method further includes moving the protrusion along the aperture such that the coupling member compresses. In another aspect of the present disclosure, the method also includes separating the first tube portion and the second tube portion.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
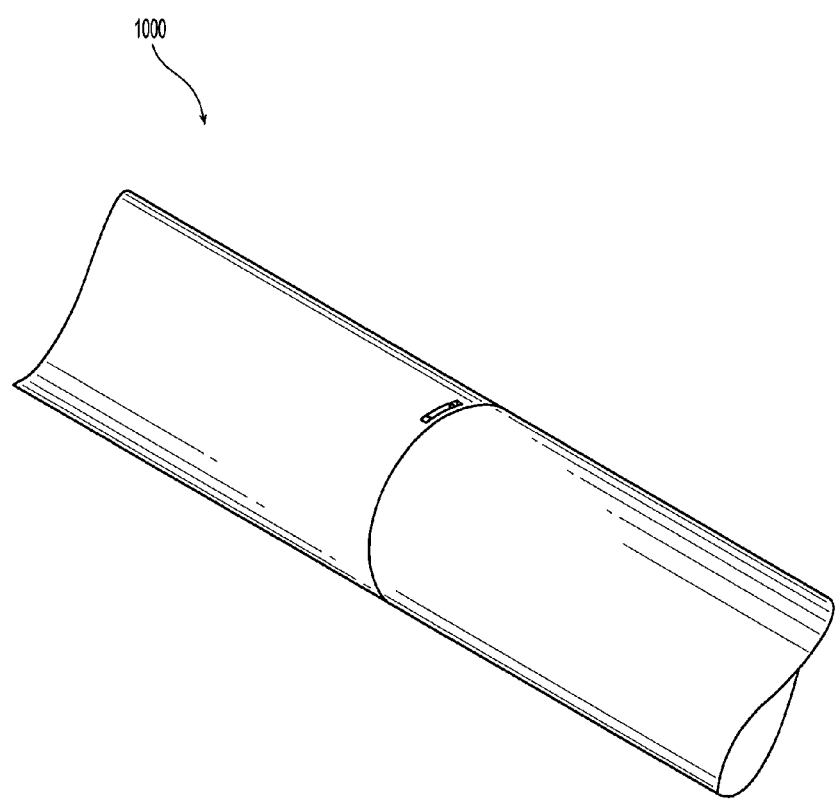
FIG. 1 is a perspective view of a portion of a medical tube assembly.

Embodiments of the presently disclosed medical tube assembly are described in detail with reference to the drawings, in which like reference numerals designate identical or corresponding elements in each of the several views. As used herein the term "distal" refers to that portion of the medical tube assembly, or component thereof, that is farther from the operator, while the term "proximal" refers to that portion of the medical tube assembly, or component thereof, that is closer to the operator.

Turning initially to FIG. 1, a medical tube assembly 1000 is shown. Medical tube assembly 1000 may have a substantially tubular profile, i.e., medical tube assembly 1000 is an elongate member with a substantially circular cross-sectional profile. In some embodiments, medical tube assembly 1000 may have other shapes, and cross-sectional profiles, e.g., square, rectangular, or ovoid. Those skilled in the art will envision other suitable shapes and configurations for medical tube assembly 1000.

Figure 2:
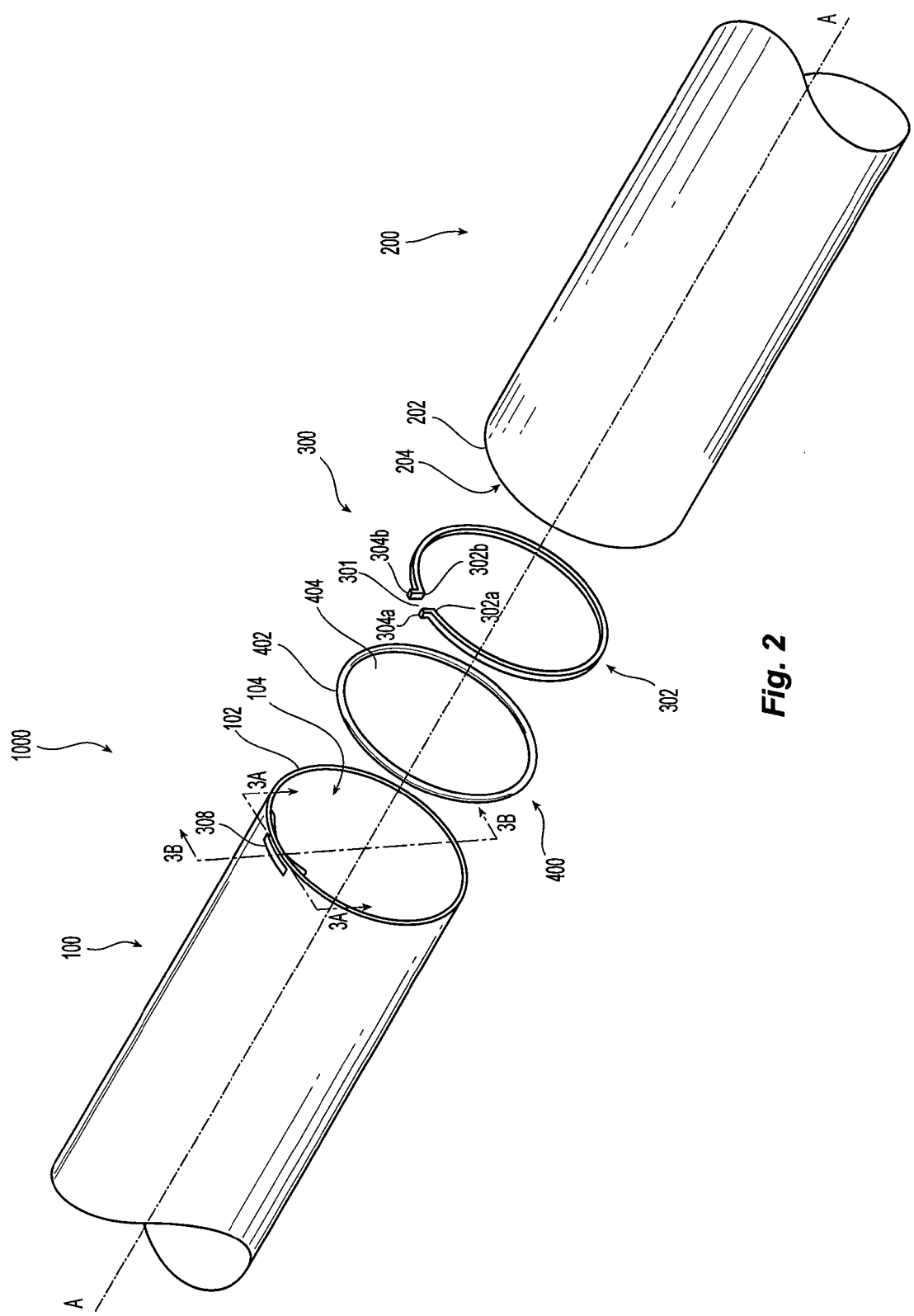
FIG. 2 is a parts-separated view of the medical tube assembly of FIG. 1.

With additional reference to FIG. 2, medical tube assembly 1000 includes a first tube portion 100, defining a longitudinal axis "A," and a second tube portion 200. First tube portion 100 and second tube portion 200 each have a substantially similar configuration, i.e., first tube portion 100 and second tube portion 200 each have a substantially tubular profile and have coupling ends 102, 202 that define respective lumens 104, 204. First tube portion 100 and second tube portion 200 are each configured to interengage, i.e., second tube portion 200 is configured for insertion into first tube portion 100, as will be described further below. Accordingly, first tube portion 100 may define a first cross-sectional diameter "D1" and second tube portion 200 may define a different second cross-sectional diameter "D2" (FIG. 4).

Medical tube assembly 1000 also includes a coupling member 300. Coupling member 300, as shown, is a substantially annular member having a discontinuity in its outer circumference, i.e., coupling member 300 has a substantially "C-shaped" configuration defining a radial gap 301 along the outer circumference of coupling member 300. Coupling member 300 includes a body 302 having a first end 302a and a second end 302b. An engagement tab 304a, 304b is disposed on each of the respective first end 302a and second end 302b of the coupling member 300. Coupling member 300 is configured to flex radially inwardly, i.e., coupling member 300 is configured such that first end 302a and second end 302b of the coupling member 300 are configured to approximate toward one another upon application of a compressive force on coupling member 300 to define a coupling condition. In this manner, radial gap 301 is redefined upon compression and expansion of the coupling member 300. Coupling member 300 also maintains a resilient bias such that, upon deformation of coupling member 300, coupling member 300 returns to the resting condition shown. Accordingly, coupling member 300 is formed of a material with a flexible configuration suitable to withstand deformation and further having resilient properties to return to a resting condition, i.e., a metal or polymeric material.

Medical tube assembly 1000 also includes a sealing member 400 configured to maintain a substantially fluid-tight environment within medical tube assembly 400, i.e., sealing member 400 is configured to minimize fluid leakage between first tube portion 100 and second tube portion 200. Sealing member 400 may have a substantially annular configuration, e.g, an annular sealing disc or an o-ring, as shown, and is configured for circumferential disposition about the second tube portion 100 and subsequent insertion into the first tube portion 100. Accordingly, sealing member 400 includes a body 402 defining an aperture 404. Aperture 404 may be dimensioned to receive a portion of second tube portion 200 such that aperture the body 402 of sealing member 400 is disposed radially between the second tube portion 200 and first tube portion 100 upon coupling, as will be described further below. As sealing member 400 is configured to be disposed within a gap defined between first tube portion 100 and second tube portion 200, the body 402 of sealing member 400 may be configured to deform to accommodate placement. Accordingly, sealing member 400 may be formed of a deformable material, i.e., a polymeric material.

Figure 3A:
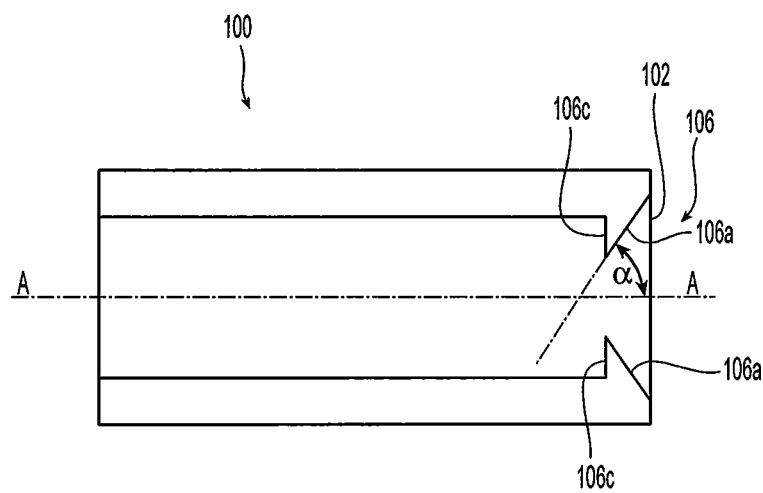
FIG. 3A is a cross-sectional view taken along section line 3A-3A of FIG. 2.
Figure 3B:
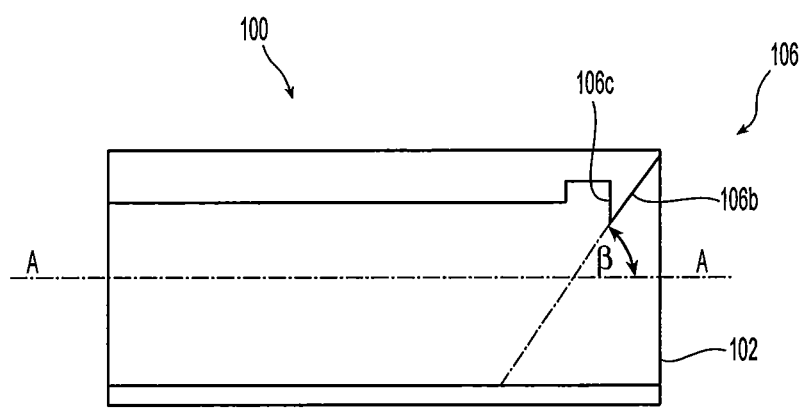
FIG. 3B is a cross-sectional view taken along section line 3B-3B of FIG. 2.
Figure 4:
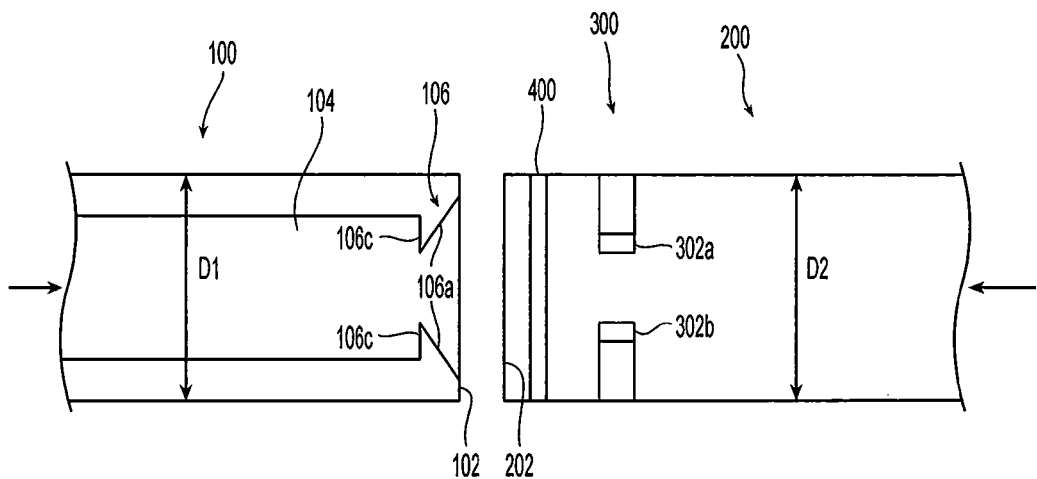
FIG. 4 is a top plan view of a first tube portion, shown in cut-away, receiving a second tube portion.

Turning now to FIGS. 3 and 4, an interior portion of the first tube portion 100 is shown in cut-away. First tube portion 100 includes a pair of interior chamfers 106 protruding radially inward from the internal surface of the first tube portion 100. Interior chamfers 106 are configured to engage a portion of the coupling member 300 (FIG. 2), as will be described further below. Accordingly, interior chamfers 106 are securely disposed on the internal surface 104 of first tube portion 100. In this manner, interior chamfers 106 may be monolithically formed with the first tube portion 100, e.g., by molding, laser cutting, or etching. In some embodiments, interior chamfers 106 may be separate components that are coupled to the internal surface of first tube portion 100, e.g., by adhesion or ultrasonic welding. In some embodiments, interior chamfers 106 may be embedded within the first tube portion 100. Interior chamfers 106 may be formed of a similar material, i.e., a polymeric material, to the remainder of first tube portion 100, or may be formed of a different material, e.g., a material having a different rigidity than the remainder of first tube portion 100. First tube portion 100 may include a pair of laterally-opposed interior chamfers 106, as shown. In some embodiments, first tube portion 100 may include a single interior chamfer 106, or more than two interior chamfers 106. In some embodiments, interior chamfers 106 may be disposed in either or both first tube portion 100 and second tube portion 200.

Interior chamfers 106 have a substantially wedge-shaped configuration, and each includes a radially inwardly-disposed surface 106a, a bottom surface 106b, and a back surface 106c. Radially-inward surface 106a, as shown, is disposed at an angle "α" with respect to the longitudinal axis "A". Distal surface 106b, as shown, is disposed at an angle "β" with respect to the longitudinal axis "A." Angles "α" and "β" may be, e.g., an oblique angle measured with respect to the longitudinal axis "A." In some embodiments, angles "α" and "β" may be substantially similar, or may be different.

Figure 5:
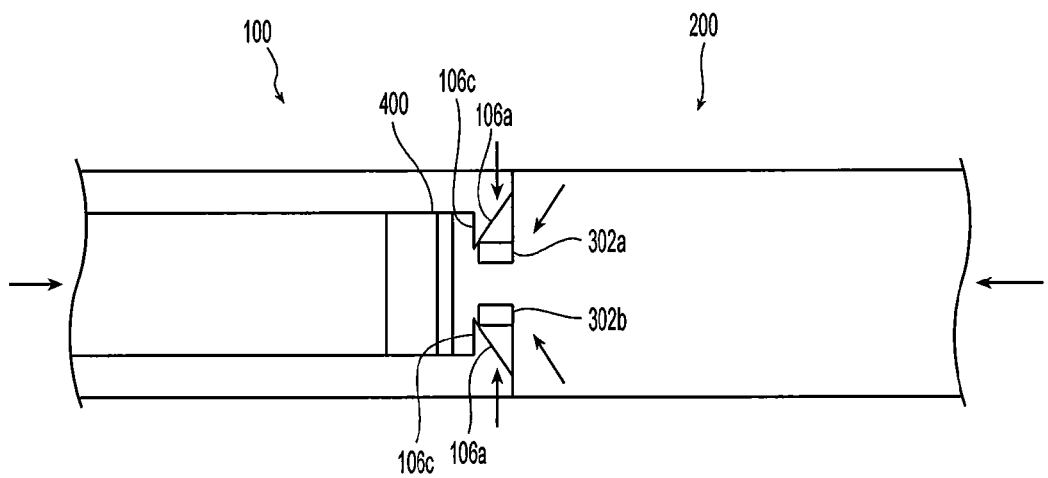
FIG. 5 is a top plan view of the first tube portion, shown in cut-away, receiving a second tube portion with the coupling member being engaged.
Figure 6:
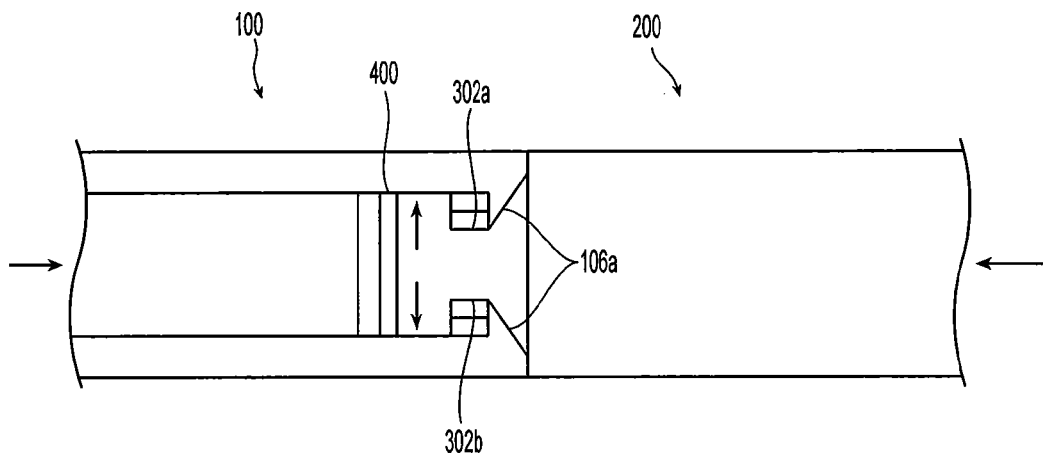
FIG. 6 is a top plan view of the first tube portion, shown in cut-away, securely coupled with the second tube portion.

Turning now to FIGS. 4, 5, and 6, coupling of the first tube portion 100 and second tube portion 200 will be described in detail. When it is desired to couple first tube portion 100 and second tube portion 200, e.g., to create an elongate tubular structure, an operator may grasp and align first tube portion 100 and second tube portion 200 into coaxial relation. The operator may then approximate first tube portion 100 and second tube portion 200 such that the coupling end 202 of the second tube portion 200 is inserted into the lumen 104 of the first tube portion 100 at the coupling end 102 of the first tube portion 100. First tube portion 100 and second tube portion 200, as described above, have diameters "D1" and "D2" and are dimensioned such that second tube portion 200 may be inserted into first tube portion 100. Accordingly, first tube portion 100 and second tube portion 200 may be dimensioned such that a tolerance, i.e., spacing is defined radially between first tube portion 100 and second tube portion 200. As the sealing member 400 is disposed about the first tube portion 100, sealing member 400 fills the space between the first tube portion 100 and second tube portion 200 such that fluid leakage between the first tube portion 100 and second tube portion 200 is minimized. Sealing member 400 may be disposed within a groove defined along the outer surface of the second tube portion 200, or may be compressively fit about the outer surface of the second tube portion 200 such that the sealing member 400 is inhibited from axial movement along the second tubular portion 200. The spacing between the first tube portion 100 and the second tube portion 200 may be minimized via forming the first tube portion 100 and second tube portion 200 with close tolerances such that the outer surface of second tube portion 200 contacts the internal surface of the first tube portion 100. Accordingly, an operator may have to provide an axially compressive force on first tube portion 100 and second tube portion 200 to overcome frictional forces generated therebetween.

As the coupling end 202 of second tube portion 200 is advanced into the lumen 104 of first tube portion 100, coupling member 300 approaches the internal chamfers 106 of first tube portion 100. In some embodiments, tabs 304a, 304b extending radially outward from the coupling member 300 may interfere with the internal surface of first tube portion 100 prior to encountering internal chamfers 106. Accordingly, an operator may deform, i.e., inwardly flex, second tube portion 200 such that tabs 304a, 304b of coupling member 300 "clear" the coupling end 102 of first tube portion 100.

Each of the tabs 304a, 304b of coupling member 300 contact each respective internal chamfer 106 of the first tube portion 100, each tab 304a, 304b cams, i.e., slides, across a respective radially-inward surface 106a and distally down the bottom surface 106b of each internal chamfer 106. Each tab 304a, 304b is configured to cam over each respective internal chamfer 106 of first tube portion 100 toward a radially-inward position. Accordingly, coupling member 300, disposed circumferentially around the second tube portion 200, exerts a compressive force on second tube portion 200.

Upon further advancement of the second tube portion 200 into first tube portion 100, each of the tabs 304a, 304b passes the respective internal chamfers 106 such that coupling member 300 returns to its resting condition under a resilient bias, i.e., tabs 304a, 304b flex radially outwardly toward their resting positions.

Figure 7:
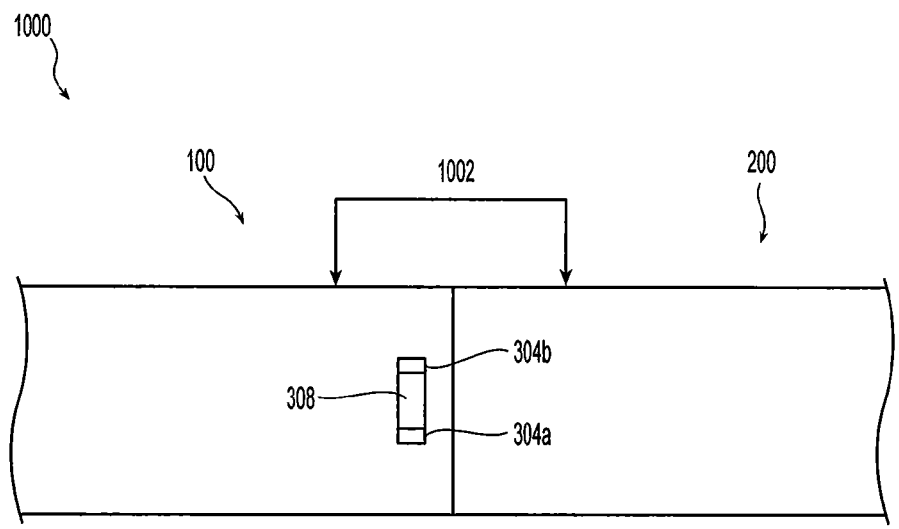
FIG. 7 is a top plan view of the medical tube assembly.
Figure 8:
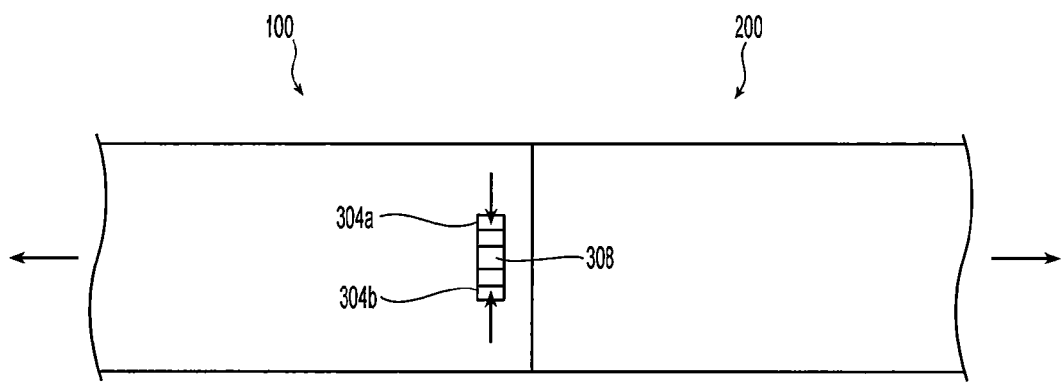
FIG. 8 is a top plan view of the medical tube assembly with the first tube portion and second tube portion being uncoupled.

Turning to FIG. 7, as tabs 304a, 304b return to their resting, radially-outward positions, tabs 304a, 304b enter the aperture 308 extending through first tube portion 100. As described above, aperture 308 is dimensioned such that tabs 304a, 304b fit snugly within aperture 308, i.e., tabs 304a, 304b are afforded minimal axial movement within aperture 308. Accordingly, aperture 308 "traps" tabs 304a, 304b such that coupling member 300 is maintained in a substantially constant axial position via the disposition of tabs 304a, 304b within aperture 308. In some embodiments, aperture 308 may be dimensioned such that tabs 304a, 304b of coupling member 300 are maintained in a slightly radially-inward position such that a compressive force is maintained about second tube portion 200 to further maintain second tube portion 200 at a substantially stationary axial position within first tube portion 100.

Accordingly, first tube portion 100 and second tube portion 200 are configured to couple via coupling member 300 from a first, separate position, to a second, locked position in which first tube portion 100 and second tube portion 200 define a coextensive region 1002 of medical tube assembly 1000. In the second, locked position shown, first tube portion 100 and second tube portion 200 are maintained in a coupled relationship in the presence of external forces, e.g., axial or torsional forces, exerted on either or both first tube portion 100 and second tube portion 200 during operation.

It may be desirable to uncouple first tube portion 100 and second tube portion 200, e.g., following use of medical tube assembly 1000, for storage purposes, or for transport. Accordingly, medical tube assembly 1000 is configured to allow an operator access to coupling member 300 from the second, unlocked condition to the first, separated condition. Aperture 308, and tabs 304a, 304b extending therethrough, are configured such that an operator may manually contact tabs 304a, 304b of coupling member 300. In some embodiments, a tool, e.g. a forceps or tweezers, may be used to contact tabs 304a, 304b of coupling member 300 through aperture 308. Tabs 304a, 304b may be forced radially inward through aperture 308 such that coupling member transitions to a radially compressed condition in which tabs 304a, 304b are cleared of the walls of aperture 308. Additionally, radial compression of the coupling member 300 may cause second tube portion to deform radially inwardly to increase the radial spacing between first tube portion 100 and second tube portion 200. In this manner, first tube portion 100 and second tube portion 200 may be separated by pulling second tube portion 200 from the lumen 104 of the first tube portion 100.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

The invention claimed is:
1. A medical tube assembly, comprising:
a first tube portion defining a longitudinal axis and including:
an enclosed aperture defining an outer perimeter and extending through the first tube portion, the enclosed aperture being spaced apart from an open end of the first tube portion; and an interior chamfer disposed on an inner surface of the first tube portion;

a second tube portion configured for insertion into the first tube portion; and a coupling member configured to couple the first tube portion and the second tube portion, the coupling member configured to circumferentially engage the second tube portion and having a pair of tabs extending radially outward, the pair of tabs configured to engage the enclosed aperture of the first tube portion, the second tube portion adapted to be inserted into the first tube portion such that the the pair of tabs engages the interior chamfer to compress the coupling member and bias the pair of tabs into the enclosed aperture.

2. The medical tube assembly of claim 1, wherein the first tube portion defines a cross-sectional diameter measured orthogonal to the longitudinal axis, and the second tube portion defines a different cross-sectional diameter measured orthogonal to the longitudinal axis.

3. The medical tube assembly of claim 2, wherein the first tube portion and the second tube portion are configured to define a coextensive region upon coupling.

4. The medical tube assembly of claim 3, wherein the pair of tabs of the coupling member is configured to be disposed along the coextensive region upon coupling.

5. The medical tube assembly of claim 1, wherein the first tube portion and the second tube portion are configured to be coupled in coaxial relation.

6. The medical tube assembly of claim 1, wherein the coupling member is configured to be radially compressed.

7. The medical tube assembly of claim 6, wherein the coupling member is configured to maintain a resilient bias toward a resting condition.

8. The medical tube assembly of claim 1, wherein the interior chamfer is oriented at an oblique angle with respect to the longitudinal axis.

9. The medical tube assembly of claim 8, wherein the interior chamfer is configured to slidably urge the pair of tabs of the coupling member in a radially inward direction.

10. The medical tube assembly of claim 1, further including a sealing member.

11. The medical tube assembly of claim 10, wherein the sealing member is configured to minimize fluid leakage between the first tube portion and the second tube portion.

12. The medical tube assembly of claim 1, wherein a tip of each tab is disposed within the enclosed aperture.

13. A method of coupling medical tubes, comprising:
providing a first tube portion defining a longitudinal axis, an interior chamfer, and an enclosed aperture in an outer wall thereof, the enclosed aperture spaced from an open end of the first tube portion;

providing a second tube portion;

providing a coupling member around the second tube portion, the coupling member including a pair of tabs extending radially outward, the pair of tabs configured to fit within the enclosed aperture;

inserting the second tube portion into the first tube portion such that the pair of tabs engage the interior chamfer to compress the coupling member and bias the pair of tabs into the enclosed aperture.

14. The method of claim 13, further comprising moving the pair of tabs along the enclosed aperture such that the coupling member compresses.

15. The method of claim 14, further comprising separating the first tube portion and the second tube portion.

16. The method of claim 13, wherein a tip of each tab is disposed within the enclosed aperture.

* * * * *